United States Patent [19]
Samuels

[11] Patent Number: 5,848,964
[45] Date of Patent: Dec. 15, 1998

[54] TEMPORARY INFLATABLE FILTER DEVICE AND METHOD OF USE

[76] Inventor: Shaun Lawrence Wilkie Samuels, 1055 Sonoma Ave., Menlo Park, Calif. 94025

[21] Appl. No.: 871,877

[22] Filed: Jun. 6, 1997

[51] Int. Cl.⁶ .................................................. A61M 29/00
[52] U.S. Cl. ............................................................ 600/200
[58] Field of Search .................................. 606/200, 194, 606/198, 191, 195; 604/104

[56] References Cited

U.S. PATENT DOCUMENTS

| | | |
|---|---|---|
| 3,952,747 | 4/1976 | Kimmell, Jr. . |
| 4,619,246 | 10/1986 | Molgaard-Nielson et al. . |
| 4,662,885 | 5/1987 | DiPisa, Jr. . |
| 4,793,348 | 12/1988 | Palmaz . |
| 5,053,008 | 10/1991 | Bajaj . |
| 5,133,733 | 7/1992 | Rasmussen et al. . |
| 5,329,942 | 7/1994 | Gunther et al. . |
| 5,397,310 | 3/1995 | Chu et al. . |
| 5,423,851 | 6/1995 | Samuels . |
| 5,549,626 | 8/1996 | Miller et al. ............................. 606/200 |
| 5,707,359 | 1/1998 | Bufalini ................................... 606/200 |

Primary Examiner—Michael Buiz
Assistant Examiner—Kevin Truong
Attorney, Agent, or Firm—Rudnick & Wolfe; William T. Rifkin; R. Blake Johnston

[57] ABSTRACT

A temporary inflatable filter device, and method of use, particularly suited to filtration of the inferior vena cava is disclosed. The device features a catheter with an inflatable cuff at one end with a mesh filter spanning the cuff's aperture. During insertion into the vena cava, the cuff is deflated and, along with the filter, is wrapped about the catheter. The catheter features a central lumen passing through its longitudinal axis. The central lumen receives a guidewire upon which the catheter may travel. Upon removal of the guidewire, the central lumen may be used as a means for delivering medicated fluids and the like into the vena cava. An inflation lumen runs parallel to the central lumen and is used for the inflation and deflation of the inflatable cuff. A filament runs through a third catheter lumen that is parallel with the other two lumina. One end of the filament is attached to the cuff while the other may be manipulated by the operator so as to allow adjustment of the orientation of the cuff and filter in the vena cava. Tensioning of the filament closes the aperture of the cuff and the opening of the filter so as to trap objects that have become lodged in the filter for removal from the vena cava.

21 Claims, 3 Drawing Sheets

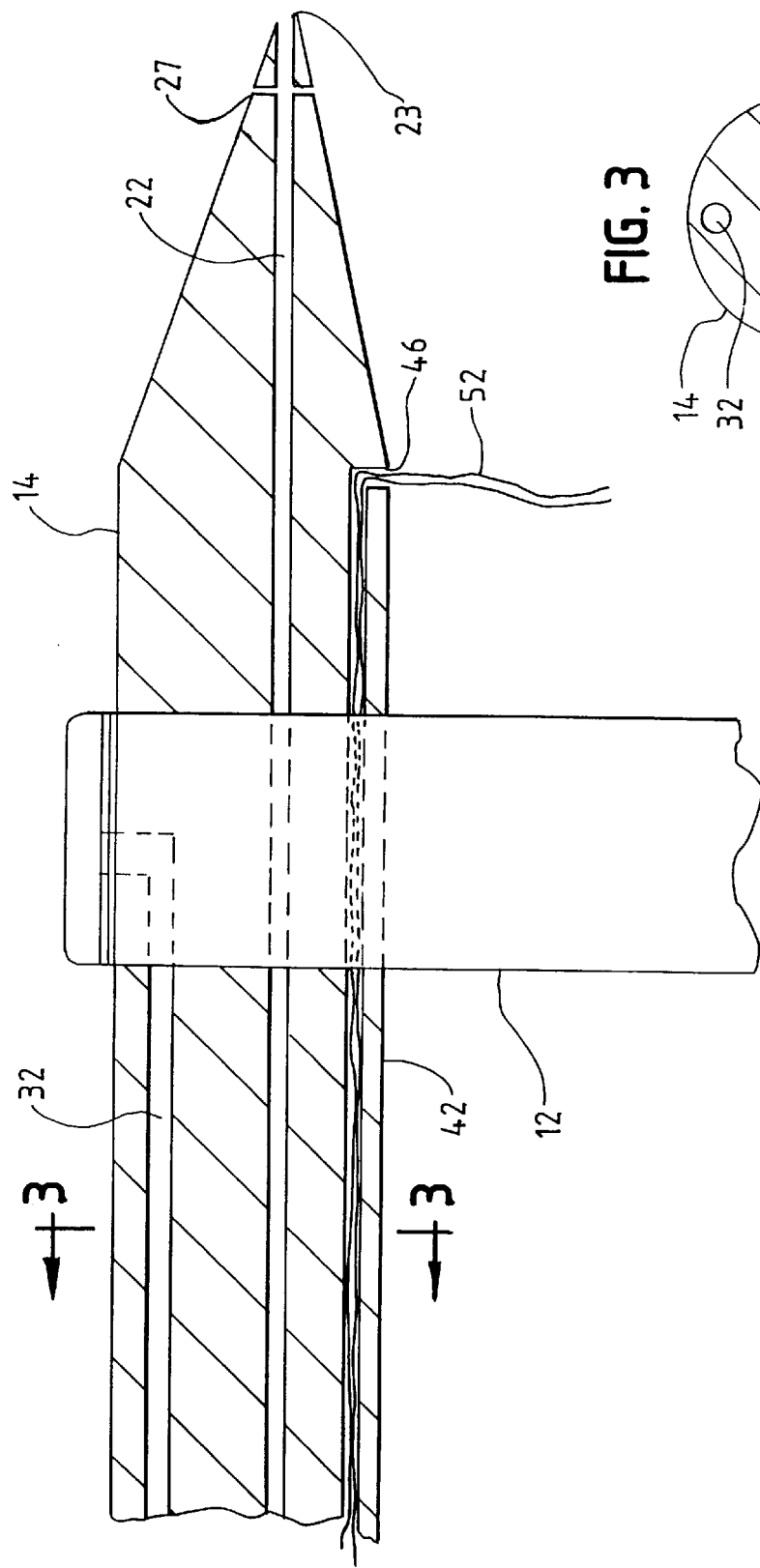

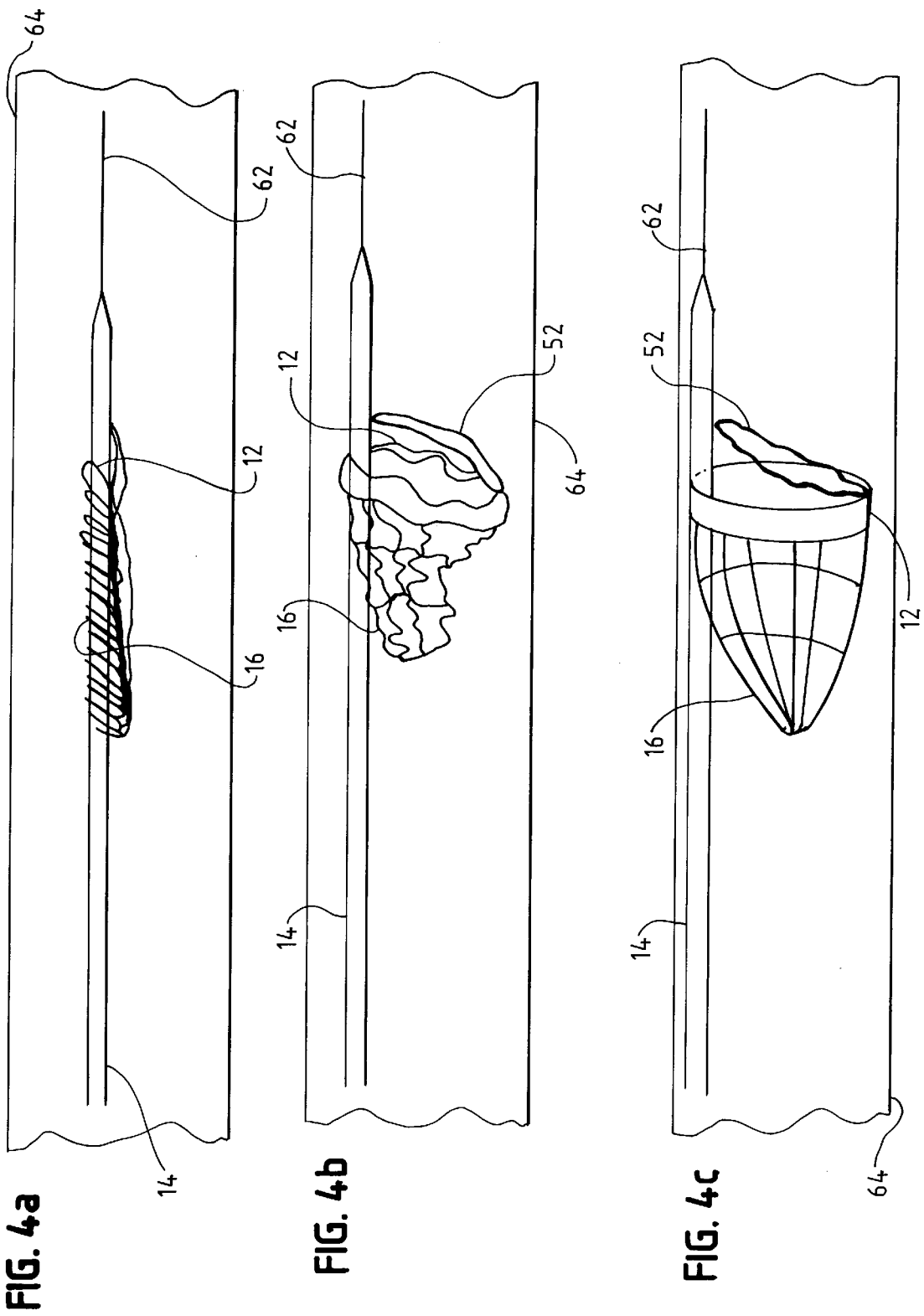

TEMPORARY INFLATABLE FILTER DEVICE AND METHOD OF USE

BACKGROUND

Patients who are temporarily immobilized because of recent surgery or trauma face an increased risk of blood clot formation in the veins of the legs. Such blood clots present significant risks to the patients' health. The most serious of these risks is the potential migration of the clots from the legs to the lungs where they may significantly compromise the blood flow to the lungs. This event, known as a pulmonary embolism, is potentially fatal and represents a leading cause of death among such patients.

In migrating from the veins of the legs to the lungs, a blood clot must travel through the inferior vena cava. This is the main vein draining the abdomen and lower extremities of the body. As a result, a number of blood filtration devices that may be positioned in the inferior vena cava have been developed.

Examples of existing vena cava filters are presented in U.S. Pat. No. 4,619,246 to Molgaard-Nielsen et al., U.S. Pat. No. 5,133,733 to Rasmussen et al. and U.S. Pat. No. 5,397,310 to Chu et al. Filters of the type disclosed by these patents all are anchored to the interior wall of the vena cava by way of metal hooks or legs. As a result, it is difficult, if not impossible, to remove such devices from the vena cava without causing severe damage to the vena cava's interior wall.

It follows that such devices must be permanently placed in the inferior vena cava without the option for retrieval even though a patient's period of risk may be limited. Health care providers using these devices thus are often faced with the difficult decision of whether to permanently implant a device, even though the period of risk is limited, or, alternatively, to allow the patient to be at risk of the occurrence of a potentially fatal event. Furthermore, in the case of patients with recent trauma or planned surgery, the health care provider will often decide against inserting a permanent device, and hence the patient is exposed to risk.

In response to this problem, devices for temporary inferior vena cava filtration have been developed. Examples of such a device is disclosed in U.S. Pat. No. 5,329,942 to Gunther et al. and U.S. Pat. No. 4,662,885 to DiPisa. While such temporary filter devices do not penetrate the interior wall of the vena cava, they are held in place by contact with it. This contact will eventually result in the filter becoming incorporated into the inferior vena cava wall via tissue ingrowth. This is undesirable for a device that is to be later removed.

In addition, U.S. Pat. No. 5,423,851 to Samuels discloses an apparatus employing an inflatable cuff to secure an endoluminal device, such as a filter, within a tubular structure of the body, such as the inferior vena cava. This apparatus is designed for the permanent placement of devices within tubular structures via radially projecting barbs and thus is not well-suited to temporary inferior vena cava filtration in its fully deployed mode. During deployment, the cuff may be temporarily affixed to the interior walls of a tubular structure while it is determined if its position is optimal. This is done by partially inflating the cuff so that it engages the interior wall of the tubular structure without its barbs being extended. As with the temporary filters discussed above, however, prolonged contact between the partially inflated cuff and the interior wall of the tubular structure, as would be required with temporary inferior vena cava filtration, would result in tissue ingrowth into the cuff. As such, the apparatus, in both its fully and partially inflated conditions, is not optimally suited to temporary inferior vena cava filtration.

Accordingly, it is an object of the present invention to provide a method and apparatus for temporary inferior vena cava filtration that is easily repositionable and removable and that minimally contacts the vessel wall.

A further disadvantage with many existing vena cava filters is that their components that engage the interior wall of the vena cava contain metal. This means that they are subject to corrosion and the influence of magnetic fields. The latter is of concern when magnetic resonance imaging, a commonly used method for visualizing structures in the body, is used. This is because metallic objects within the patient's body may respond to the strong magnetic field used by such imaging. As such, devices that use metal components to hold them in place within the body, such as existing vena cava filters, may change position when subjected to such magnetic fields. This can have catastrophic results. It is thus a further object of the invention to provide a temporary filtration device that does not contain any metal in the component engaging the interior wall of the vena cava.

Another disadvantage of existing vena cava filters is that they do not allow infusion of fluids, medications, contrast media or other agents once the filters have been positioned within the vessel. The ability to deliver contrast media is important in assessing the presence of blood clots within the filter after its placement in the vessel. Furthermore, if a clot is present, the option of delivering pharmacologic agents for dissolving the clot is desirable to. In addition, it is desirable have the capability to deliver maintenance intravenous fluids, such as those containing heparinized saline, so as to prevent the propagation of a clot that may have been trapped by the filter, and to prevent the development of a clot on the filter device itself. As such, it is a further object of the invention to provide a filtration device through which fluids may be injected.

Existing vena cava filter devices also do not provide a means for adjusting the orientation or size of the filter opening once the filter is positioned within the vessel. Such features would be invaluable in allowing the device to be used to retrieve a trapped clot. First, the filter opening could be oriented to capture the clot. Next, after the clot was captured within the filter, the opening of the filter could be cinched so as to create a purse string like closure of the filter mesh element thus trapping the clot. The clot then could be removed with the filter. It is thus a further object of the invention to provide a filtration device that offers a means of adjusting the orientation and size of the filter opening.

SUMMARY

The present invention is directed to a temporary inflatable filter device and a method for using it to provide filtration within a tubular structure in the human body, such as the inferior vena cava. The device features a catheter having a proximal portion and a distal portion. A central lumen extends along the longitudinal axis of the catheter and opens into ports in the proximal and distal portions of the catheter. As a result, the central lumen receives a guidewire along which the catheter may travel. The proximal port of the central lumen may be configured so as to receive a syringe so that fluids containing medication and the like may be injected through the central lumen and into the tubular structure after the guidewire is removed.

The catheter also has an inflation lumen extending longitudinally through it and opens into ports in the proximal and distal portions of the catheter. The distal port of the inflation lumen is in fluid communication with an inflatable cuff while the proximal port is connected to a means for inflating the cuff with inflation material. The inflatable cuff has a generally hollow cylindrical configuration with a relatively large central aperture. The cuff is permanently attached to the distal end of said catheter so that when the cuff is in an inflated condition, the catheter may be used to hold it in position within the tubular structure. This results in minimal contact between the cuff and the interior wall of the tubular structure. A mesh filter is attached by its opening to the inflatable cuff so that when the inflatable cuff is inflated, any fluid traveling through the central aperture of the cuff must pass through the mesh filter.

A cuff-positioning string lumen also extends longitudinally through the catheter and generally runs parallel to the other two lumina. A filament is disposed within the cuff-positioning string lumen and one end extends out of the proximal portion of the catheter while the other end extends out of the distal portion of the catheter. The distal end of the filament is attached to the inflatable cuff so that manipulation of the filament adjusts the orientation of the inflatable cuff within the tubular structure. Furthermore, tensioning the filament contracts the central aperture of the cuff, and thus the opening of the mesh filter, so as to trap any objects lodged within the mesh filter.

When it is desired to remove the mesh filter, the cuff is deflated by the withdrawal of the inflation material through the inflation lumen and the catheter, along with the cuff, mesh filter and any objects trapped therein, are withdrawn from the tubular structure.

For a more complete understanding of the nature and scope of the invention, reference may now be had to the following detailed description of embodiments thereof taken in conjunction with the appended claims and accompanying drawings.

BRIEF DESCRIPTION OF THE DRAWINGS

FIG. 2 is a cross-sectional view of the catheter of the device of FIG. 1 taken down its longitudinal axis;

FIG. 3 is a cross-sectional view of the catheter of FIG. 2 taken along line 3—3; and FIGS. 4a through 4c show in cross-section a blood vessel with an elevational view of the device of FIG. 1 being deployed therein in accordance with the method of the present invention.

DESCRIPTION

Figure 1:
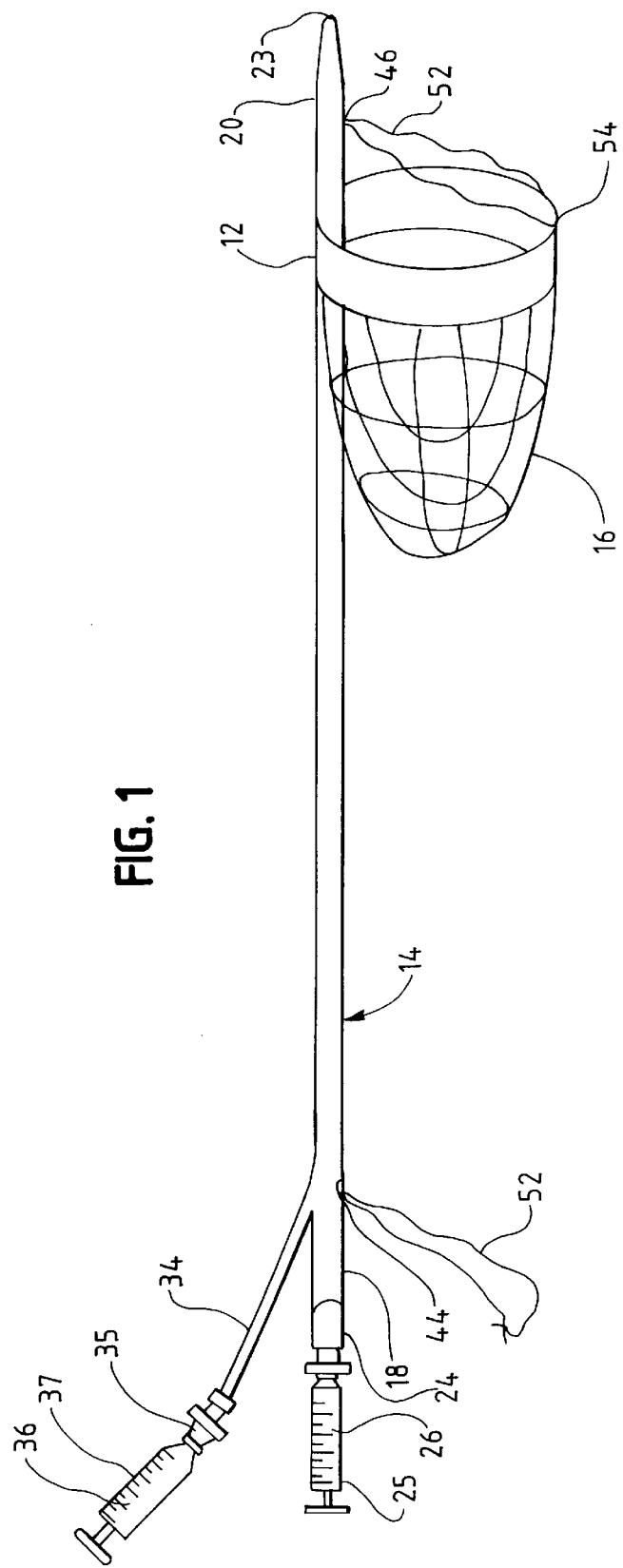
FIG. 1 is a perspective view of an embodiment of the device of the present invention with the inflatable cuff in an inflated condition.

Referring to FIG. 1, an embodiment of the temporary inflatable filter device of the present invention is shown. The device, shown in its inflated and deployed configuration, features an inflatable cuff 12 attached by its inner surface to a catheter, indicated generally at 14. Also connected about the inner surface of cuff 12 is mesh filter 16. Catheter 14 features proximal portion 18 and distal portion 20.

Cuff 12 is composed of bioinert, polymeric plastic, and is of a cylindrical shape with a comparatively large central aperture surrounded by the relatively thin inflatable element. In this way, the profile of the deployed cuff creates the least possible impediment to flow through the vessel in which the filter is deployed. When deployed, the inflated cuff 12 is disposed transversely within a vessel lumen, juxtaposed circumferentially to the interior wall of the vessel, although not necessarily circumferentially contacting the wall. The cuff diameter is preferably approximately equal to that of the normal human inferior vena cava.

Filter 16 features mesh netting which may be constructed of either plastic or metallic strands. Filter 16 is secured to the circumference of the inner surface of cuff 12 by a biologically inert adhesive.

Catheter 14 is constructed of a polymeric plastic which is bioinert and, as shown in FIGS. 2 and 3, features a plurality of lumina. Each lumen of the preferred embodiment will be discussed separately.

Central lumen 22 has multiple purposes. As shown in FIGS. 2 and 3, this lumen passes through the center of catheter 14, coaxial with the longitudinal axis of the catheter, and is of sufficient diameter to accommodate a guidewire of at least 0.035 inch diameter. As shown in FIG. 1, central lumen 22 opens into a port 24 affixed at the proximal end 18 of catheter 14. Port 24 remains outside of the patient's body and accepts a standard syringe 25. As such, central lumen 22 may be used for the injection of fluids or medication 26 after the guidewire is removed therefrom. Port 24 may optionally be implanted in the patient, along with the necessary attachments, so as to allow continuous administration of fluids to the filter site.

Central lumen 22 is of consistent diameter throughout its length. The distal portion 20 of catheter 14 undergoes a concentric gentle tapering to a size only slightly larger than central lumen 22 at its tip 23. Such tapering takes place approximately starting from the point of departure of the other two lumina, to be discussed below. Preferably, a series of small side-holes, indicated at 27 in FIG. 2, leading from central lumen 22 to the surface of catheter 14 are disposed through the tip 23. The presence of side-holes 27 allows for easier passage of fluids through the catheter, and makes it less likely that the central lumen will be occluded by clots, deposits, or by contact with the vessel wall.

An inflation lumen, indicated at 32 in FIGS. 2 and 3, is disposed parallel to central lumen 22, and is used for inflation and deflation of cuff 12. This lumen may be of any size that allows cuff 12 to be easily inflated or deflated and is generally of consistent diameter throughout the length of catheter 14. As shown in FIG. 2, one end of inflation lumen 32 terminates at a junction with cuff 12 so that inflation lumen 32 and cuff 12 are in fluid communication with one another.

As shown in FIG. 1, the other end of inflation lumen 32 emerges as side-arm port 34 from the catheter 14 at a location external to the body of the patient. Both the angle of departure and length of side-arm port 34 may be variable. During manufacture, side-arm port 34 and catheter 14 may be molded from a single piece or, alternatively, side-arm port 34 may be bonded to catheter 14. Preferably, side-arm port 34 features a check valve 35. Side-arm port 34 allows passage of inflation material 36 into inflation lumen 32 via injection with a standard syringe 37. While syringe 37 is attached to side-arm port 34, valve 35 allows inflation material 36 to flow either into or out of inflation lumen 32 so that cuff 12 may be either inflated or deflated. When cuff 12 is inflated and syringe 37 is removed, valve 35 in side-arm port 34 closes by spring action and prevents inflation material 36 from escaping. As a result, cuff 12 is maintained in an inflated state. As an alternative to the check valve arrangement, a standard luer-lock may be used in valve 35.

The inflation material for the cuff may be any biocompatible, non-viscous fluid which may be easily introduced and withdrawn in the aforementioned fashion. In the preferred embodiment, the fluid introduced into cuff 12 is a mixture of saline solution and radio-opaque contrast media so that cuff 12 may be easily visualized under fluoroscopy, the generally accepted imaging technique used in the placement of such intraluminal devices. The radio-opaque contrast, it should be noted, is designed for intravenous injection, and may also be well seen under other imaging techniques such as plain film radiography, computed tomography (CT) and magnetic resonance imaging (MRI).

The cuff-positioning string lumen, shown at 42 in FIGS. 2 and 3, is disposed parallel to the other two lumina and, in the preferred embodiment, extends along the opposite side of central lumen 22 from inflation lumen 32. As shown in FIG. 1, one end of cuff-positioning string lumen 42 terminates at proximal end 18 of syringe 14 in a standard syringe-compatible hub 44. Like port 24 and side-arm port 34, hub 44 remains external to the patient's body. The lumen extends at a generally uniform diameter through catheter 14 and terminates at an opening 46 in distal portion 20.

A small gauge filament, indicated at 52, is constructed of either non-thrombogenic wire or string. It extends the length of cuff-positioning string lumen 42 and emerges from hub 44 and opening 46, the latter of which is near cuff 12. Filament 52 exits opening 46 as a loop and is attached to the circumference of cuff 12 at point 54 which is the furthest distance from catheter 14. Alternatively, filament 52 may be attached at multiple points along the circumference of cuff 12.

The portion of filament 52 exiting hub 44, since it is external to the patient's body, may be manipulated by the operator. By applying tension to filament 52, and thus the filament loop attached to cuff 12, the orientation of cuff 12 may be altered within the blood vessel lumen as the cuff, in effect, pivots about the junction between cuff 12 and catheter 14. As such, the aperture of cuff 12 and the opening of filter 16 can be positioned so as to be perpendicular to the axis of blood flow within the blood vessel. Furthermore, continued tension on filament 52 reduces the aperture of cuff 12, and thus the opening of filter 16, in a purse-string fashion, especially when cuff 12 is deflated. This allows clot capture and entrapment within filter 16. As such, the clot may then be removed from the patient's body along with filter 16. In the absence of clots, tensioning of filament 52 collapses cuff 12 after it has been deflated using inflation lumen 32. This facilitates removal of catheter 14 from the blood vessel and the patient's body.

FIGS. 4a through 4c illustrate the steps to be performed in deploying the inflatable temporary filter device of the present invention. Initially, catheter 14, with filter 16 and deflated cuff 12 wrapped around it, is loaded over a previously placed guidewire 62, via guidewire lumen 22, and is fed through the venous access site. The venous access site is essentially an incision in the patient's skin that leads to the desired blood vessel. The wrapped catheter may optionally be delivered through a vascular access sheath at the access site. Preferred access sites include the jugular veins, the subclavian veins, and the femoral veins. The length of guidewire 62 is such that a sufficient portion of it emerges from the access site so as to allow the entire length of catheter 14 to be loaded onto guidewire 62, externally from the patient's body, with a portion of guidewire 62 remaining after port 24 for the operator to grip as catheter 14 is being advanced to its final position.

As shown in FIG. 4a, once catheter 14 is inserted through the venous access site, it is positioned at the desired point within inferior vena cava 64. Inflation material is then injected into cuff 12 via inflation lumen 32 as illustrated in FIG. 4b. After cuff 12 is fully inflated, as shown in FIG. 4c, the orientation of its aperture and the opening of filter 16 may be adjusted via filament 52 as discussed above. Catheter 14 remains in place with cuff 12 attached to hold cuff 12 and filter 16 in position within inferior vena cava 64. When filtering is no longer required, or a blood clot has been captured within filter 16, cuff 12 may be deflated through inflation lumen 32 and collapsed via filament 52 for withdrawal from the patient's body along with catheter 14 via the venous access site.

While the primary purpose of the present invention is temporary inferior vena cava filtration, the same elemental structure of the device may be used in a variety of other capacities in other tubular structures within the human body. Examples of these include the use of the invention as a method and apparatus for retrieving foreign bodies from any tubular structure within the body and as a method and apparatus for the extraction of stones from the biliary tree or urinary tract. The use of the device of the present invention in such capacities would require only slight alterations in the sizes and configurations of the elements presented.

While the preferred embodiments of the invention have been shown and described, it will be apparent to those skilled in the art that changes and modifications may be made therein without departing from the spirit of the invention, the scope of which is defined by the appended claims.

What is claimed is:

1. A temporary filter device for providing filtration within a tubular structure in the human body comprising:
   a) a catheter having a longitudinal axis, a proximal portion and a distal portion;
   b) said catheter having an inflation lumen extending longitudinally therethrough with ports in the proximal and distal portions of the catheter;
   c) an inflatable cuff of generally hollow cylindrical configuration, said cuff directly permanently attached near to the distal end of said catheter so that when said cuff is in an inflated condition, the catheter may be used to hold the cuff in position within the tubular structure so that cuff contact with the tubular structure is minimized;
   d) said cuff in fluid communication with the inflation lumen port in the distal portion of the catheter;
   e) a filter attached to the inflatable cuff for deployment when said cuff is inflated so that any fluid traveling past the cuff passes through the filter;
   f) means for inflating and deflating the cuff with inflation material; and
   g) a valve for maintaining said cuff in an inflated condition for a desired time period.

2. The temporary filter device of claim 1 further comprising:
   a) a cuff-positioning string lumen extending longitudinally through said catheter;
   b) a filament slidably disposed within the cuff-positioning string lumen and having a proximal end extending out of the proximal portion of the catheter and a distal end extending out of the distal portion of the catheter;
   c) said distal end of said filament attached to said inflatable cuff so that manipulation of the proximal end of said filament permits adjustment of the orientation of said inflatable cuff within said tubular structure including the ability to cinch the filter in a purse-string fashion so as to trap an object lodged within the mesh filter for subsequent removal.

3. The temporary filter device of claim 2 wherein the filament is composed of a bio-inert, non-thrombogenic material.

4. The temporary filter device of claim 1 further comprising a central lumen extending through said catheter coaxially with the longitudinal axis of said catheter and having ports in the proximal and distal portions of the catheter so that said central lumen may slidingly receive a guidewire along which said catheter may travel.

5. The temporary filter device of claim 4 wherein a proximal port of central lumen is adapted to receive a syringe so that fluid may be injected through the central lumen and into the tubular structure.

6. The temporary filter device of claim 5 wherein the fluid includes radiopaque contrast media.

7. The temporary filter device of claim 4 further comprising at least one side-hole through the distal portion of said catheter, said side-hole in fluid communication with said central lumen.

8. The temporary filter device of claim 1 wherein the catheter is constructed of bio-inert, non-thrombogenic materials.

9. The temporary filter device of claim 1 wherein the inflatable cuff is constructed of bio-inert, non-thrombogenic materials.

10. The temporary filter device of claim 1 wherein said mesh filter is constructed of bio-inert, non-thrombogenic materials.

11. The temporary filter device of claim 1 wherein said inflation material includes a biocompatible non-viscous fluid.

12. The temporary filter device of claim 11 wherein said inflation material includes radiopaque contrast media.

13. The temporary filter device of claim 1 wherein the distal portion of the catheter is tapered.

14. The temporary filter device of claim 1 wherein the means for inflating the cuff is a syringe.

15. A temporary filter device for providing filtration within a tubular structure in the human body comprising:

a) a catheter having a longitudinal axis, a proximal portion and a distal portion;

b) said catheter having a central lumen extending therethrough coaxially with the longitudinal axis of said catheter and having ports in the proximal and distal portions of the catheter so that said central lumen may slidingly receive a guidewire along which said catheter may travel;

c) said catheter having an inflation lumen extending longitudinally therethrough with ports in the proximal and distal portions of the catheter;

d) an inflatable cuff of generally hollow cylindrical configuration, said cuff directly permanently attached near to the distal end of said catheter so that when said cuff is in an inflated condition, the catheter may be used to hold the cuff in position within the tubular structure so that cuff contact with the tubular structure is minimized;

e) said cuff in fluid communication with the inflation lumen port in the distal portion of the catheter;

f) a filter attached to the inflatable cuff for deployment when said cuff is inflated so that any fluid traveling past the cuff passes through the filter;

g) means for inflating and deflating the cuff with inflation material through the inflation lumen port; and h) a valve for maintaining said cuff in an inflated condition for a desired time period.

16. The temporary filter device of claim 15 further comprising:

a) a cuff-positioning string lumen extending longitudinally through said catheter;

b) a filament slidably disposed within the cuff-positioning string lumen and having a proximal end extending out of the proximal portion of the catheter and a distal end extending out of the distal portion of the catheter;

c) said distal end of said filament attached to said inflatable cuff so that manipulation of the proximal end of said filament permits adjustment of the orientation of said inflatable cuff within said tubular structure including the ability to contract so as to trap an object lodged within the filter.

17. The temporary filter device of claim 15 wherein said inflation material includes a biocompatable non-viscous fluid.

18. The temporary filter device of claim 17 wherein said inflation material includes radiopaque contrast media.

19. The temporary filter device of claim 15 wherein a proximal port of the central lumen is adapted to receive a syringe so that a fluid may be injected through the central lumen and into the tubular structure.

20. The temporary filter device of claim 15 further comprising at least one side-hole through the distal portion of said catheter, said side-hole in fluid communication with said central lumen.

21. The temporary inflatable filter device of claim 15 wherein the distal portion of the catheter is tapered.

\* \* \* \* \*